United States Patent
Landes et al.

(10) Patent No.: US 11,513,335 B2
(45) Date of Patent: Nov. 29, 2022

(54) ENDOSCOPE HAVING A CIRCUIT BOARD

(71) Applicant: HOYA CORPORATION, Tokyo (JP)

(72) Inventors: Hermann Landes, Friedberg (DE); Tilman Schröter, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 37 days.

(21) Appl. No.: 17/282,568

(22) PCT Filed: Oct. 24, 2019

(86) PCT No.: PCT/IB2019/001085
§ 371 (c)(1),
(2) Date: Apr. 2, 2021

(87) PCT Pub. No.: WO2020/084341
PCT Pub. Date: Apr. 30, 2020

(65) Prior Publication Data
US 2021/0341726 A1   Nov. 4, 2021

(30) Foreign Application Priority Data
Oct. 26, 2018   (DE) .................... 10 2018 126 795.9

(51) Int. Cl.
*G02B 23/24*   (2006.01)
*H04N 5/225*   (2006.01)

(52) U.S. Cl.
CPC ....... *G02B 23/2484* (2013.01); *G02B 23/243* (2013.01); *H04N 5/2251* (2013.01); *H04N 2005/2255* (2013.01)

(58) Field of Classification Search
CPC .............. G02B 23/2484; G02B 23/243; H04N 5/2251; H04N 2005/2255; A61B 1/0684; A61B 1/07; A61B 1/00096; A61B 1/0011; A61B 1/051
See application file for complete search history.

(56) References Cited

U.S. PATENT DOCUMENTS

| | | | |
|---|---|---|---|
| 2002/0080233 | A1 | 6/2002 | Irion et al. |
| 2008/0091064 | A1 | 4/2008 | Laser |
| 2009/0021618 | A1 | 1/2009 | Schwarz et al. |
| 2011/0118549 | A1 | 5/2011 | Han |

(Continued)

FOREIGN PATENT DOCUMENTS

| | | |
|---|---|---|
| DE | 10 2017 102 178 B3 | 6/2018 |
| EP | 1 182 959 B1 | 1/2003 |

(Continued)

OTHER PUBLICATIONS

U.S. Appl. No. 17/282,576 to Anh Minh Do, which was filed on Apr. 2, 2021.

(Continued)

*Primary Examiner* — Shadan E Haghani
(74) *Attorney, Agent, or Firm* — Greenblum & Bernstein, P.L.C.

(57) ABSTRACT

The present invention relates to an endoscope including an object, which is to be supplied with electric current, in an endoscope head of the endoscope, and a circuit board for the object to be supplied with electric current. The circuit board extends from the object, which is to be supplied with electric current, in the distal direction of the endoscope head.

8 Claims, 12 Drawing Sheets

(56) References Cited

U.S. PATENT DOCUMENTS

| | | |
|---|---|---|
| 2013/0271588 A1* | 10/2013 | Kirma .................. A61B 1/05 348/76 |
| 2014/0210976 A1 | 7/2014 | Lin |
| 2016/0270631 A1 | 9/2016 | Kirma et al. |
| 2018/0070803 A1 | 3/2018 | Mikami |
| 2019/0328214 A1 | 10/2019 | Do |
| 2020/0008659 A1 | 1/2020 | Viebach et al. |
| 2020/0178770 A1 | 6/2020 | Do |
| 2020/0178779 A1 | 6/2020 | Komoro |

FOREIGN PATENT DOCUMENTS

| | | |
|---|---|---|
| EP | 2 018 043 A1 | 1/2009 |
| EP | 2 648 602 B1 | 7/2018 |
| JP | 2004361595 A * | 12/2004 |
| JP | 2007-229085 A | 9/2017 |

OTHER PUBLICATIONS

International Search Report issued in International Patent Application No. PCT/IB2019/001085, dated Jan. 23, 2020, along with an English translation thereof.

Written Opinion of the International Searching Authority issued in International Patent Application No. PCT/IB2019/001085, dated Jan. 23, 2020, along with an English translation thereof.

* cited by examiner

ENDOSCOPE HAVING A CIRCUIT BOARD

The present invention relates to an endoscope comprising an object, which is to be supplied with electric current, in an endoscope head of the endoscope, and a circuit board for the object to be supplied with electric current.

A camera and an illumination means for illuminating and for capturing images of a region to be viewed by the endoscope are arranged in a known endoscope at the distal end of the endoscope head. Both the camera and the illumination means are supplied with electric current.

Due to the small size of an endoscope head, there is always a need to save space in order to accommodate the required components advantageously in a small space.

Therefore, it is the object of the invention to provide an endoscope in which the components of the endoscope head are installed in an advantageous and space-saving manner but still allow a favorable mode of operation.

This object is achieved by an endoscope comprising the features of claim 1.

Advantageous developments are the subject matter of the dependent claims.

The invention relates to an endoscope comprising an object, which is to be supplied with electric current, in an endoscope head of the endoscope, and a circuit board for the object to be supplied with electric current. The circuit board extends from the object to be supplied with electric current in the distal direction of the endoscope head.

Thus, the circuit board is formed into the distal direction from the object to be supplied with electric current. The region proximally from the object to be supplied with electric current is not occupied by the circuit board and can be used for other purposes.

The object to be supplied with electric current can be arranged on the circuit board. As an alternative, the object to be supplied with electric current can be spaced apart from the circuit board but is supplied with current via the circuit board.

The circuit board can extend to a location distally from the object to be supplied with electric current. Thus, the circuit board can protrude beyond the object to be supplied with electric current in the distal direction. The region distally from the object to be supplied with electric current can be used for the circuit board.

The circuit board can be folded, and at least one portion of the circuit board can be located proximally from the object to be supplied with electric current. The circuit board can also be bent or wound.

The object to be supplied with electric current can be an image sensor for capturing an image. The object to be supplied with electric current can be another electric or electronic member which is supplied with electric current by means of a circuit board.

The endoscope can have a lens arranged on the distal side of the object to be supplied with electric current, the circuit board at least partly surrounding the lens. Thus, the circuit board can even stabilize the lens.

The circuit board can protrude beyond the lens in the proximal direction. The circuit board can form an optical shielding between the lens and a light source that acts on the distal end of the endoscope head to shield a light irradiation of the light source to the lens.

The circuit board can include a main portion for the object to be supplied with electric current, and an edge portion. The edge portion can be connected to the main portion on a fold edge. The edge portion can include an end portion on the side opposite the main portion, the end portion being folded such that it is in contact with the main portion to form an electronic shielding.

The edge portion and the main portion can form a closed circle in cross-section, and they can extend around a lens mounting.

The circuit board can form a housing of the endoscope head.

In the present invention, a circuit board for an object to be supplied with electric current can therefore be used for versatile purposes. The circuit board are assigned functions such as protecting, supporting, holding elements that are at least partly surrounded by the circuit board.

The above-described aspects of the present invention can be suitably combined.

Below, the present invention is described in detail with reference to the drawings on the basis of embodiments.

FIRST EMBODIMENT

Referring to FIGS. 1 to 9, a first embodiment of the present invention is described below.

Figure 1:
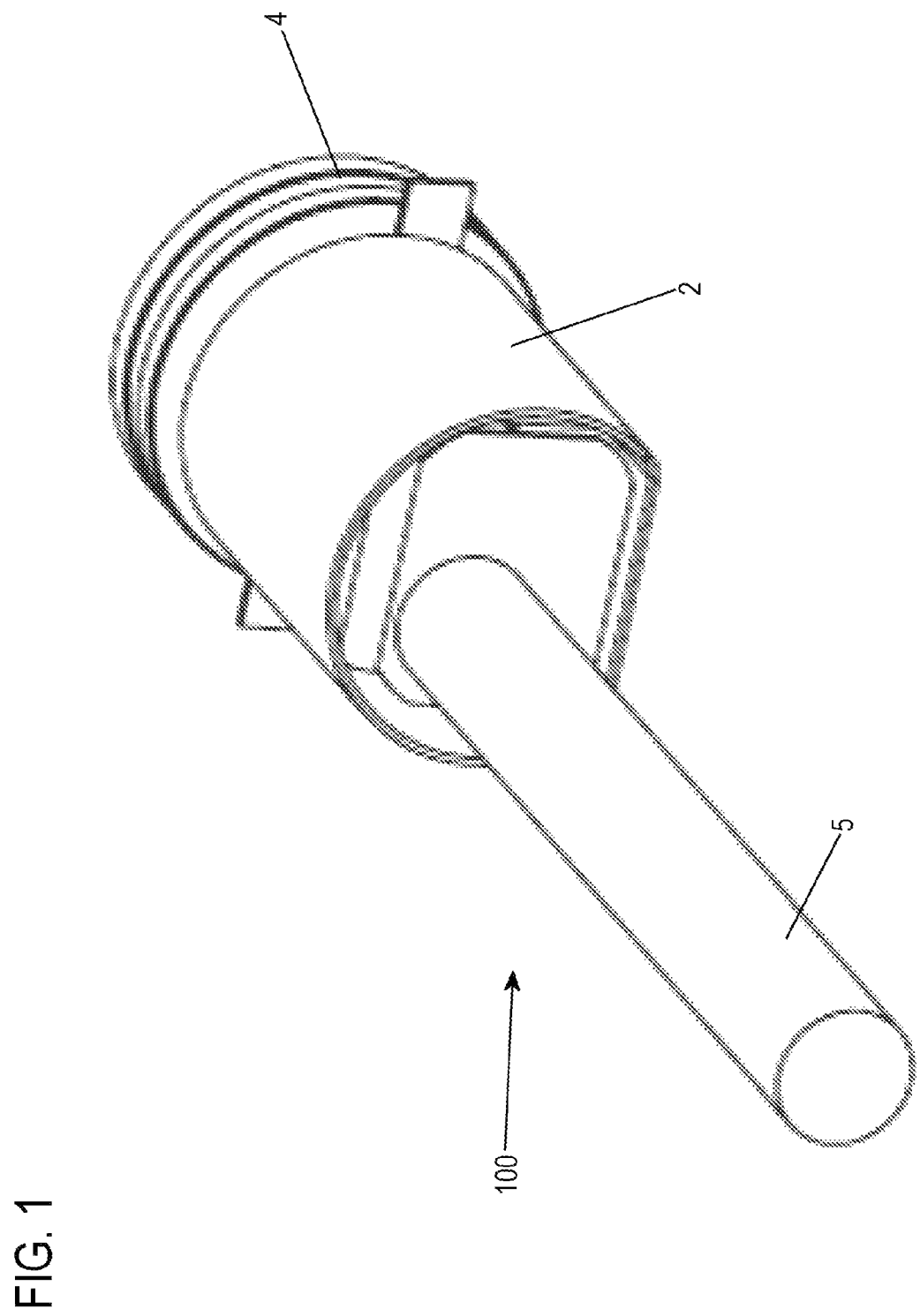
FIG. 1 shows a schematic perspective view of an endoscope head of a first embodiment of the present invention.

FIG. 1 shows an endoscope head 100 of the first embodiment of the present invention. The endoscope head 100 has a light source not shown, such as an LED or a fiber optic cable (glass fiber cable) as a light guide, and a lens 4 on the distal side. The light source emits light to a region to be monitored by the endoscope. The light reflected by the region to be monitored is guided via the lens 4 to a camera (image sensor 1) explained below, by which the image information is transmitted.

A system cable 5 coming from the proximal side of the endoscope can be used to transmit image information, for power supply of the LED and/or camera, etc.

The endoscope head includes a circuit board 2 for at least one object to be supplied with electric current (simply referred to as "object" hereinafter). Said object can be arranged on the circuit board 2 itself or spaced apart from the circuit board 2. The circuit board 2 has conducting paths for the object. Further electrical components, such as capacitors, Hall elements, electrical resistances, coils, diodes, transistors and integrated circuits, can be arranged as objects on the circuit board 2.

The circuit board 2 is a folded circuit board and is described in more detail below.

Figure 2:
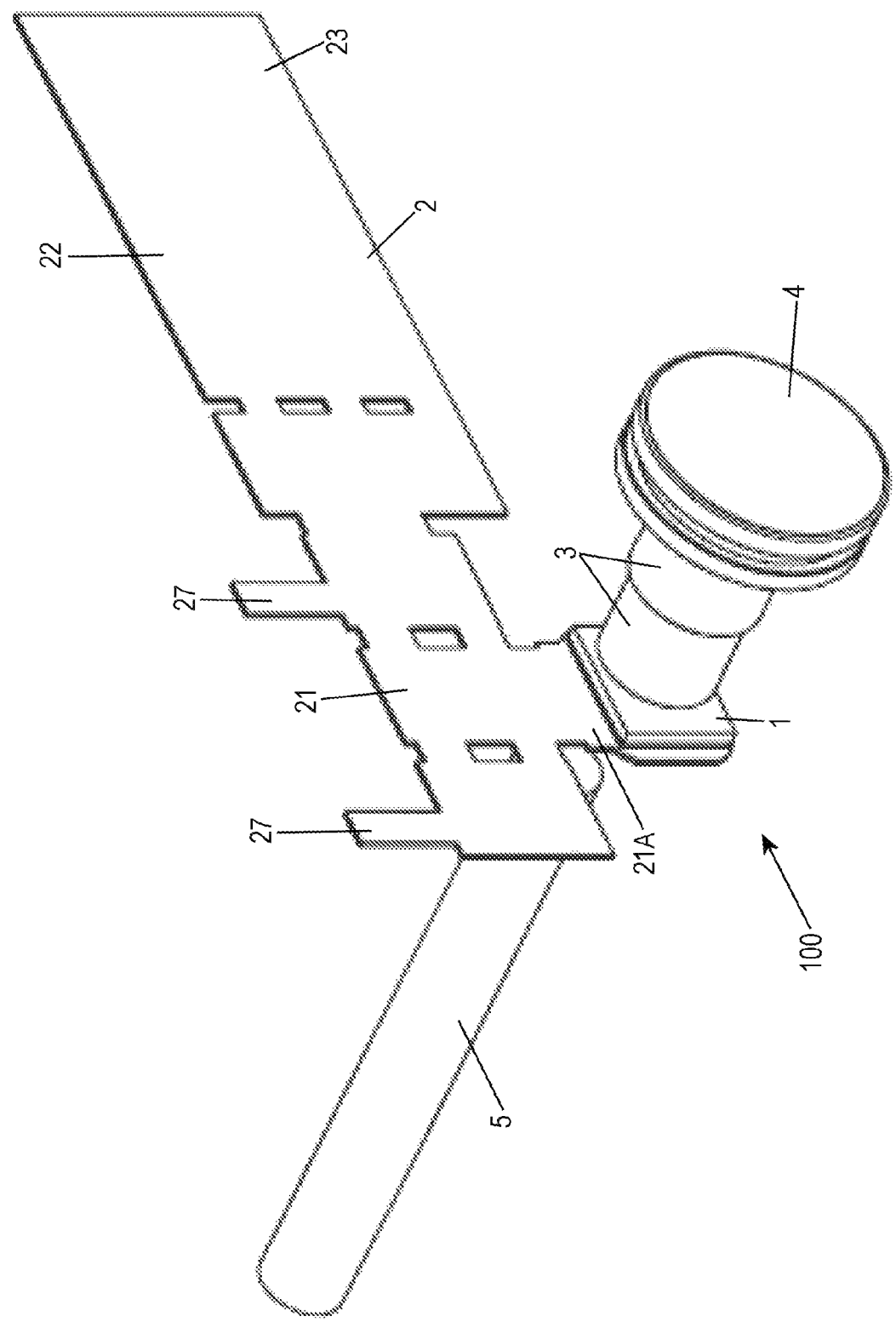
FIG. 2 shows a schematic perspective view of the endoscope head of the first embodiment from the distal side with the circuit board unfolded.
Figure 3:
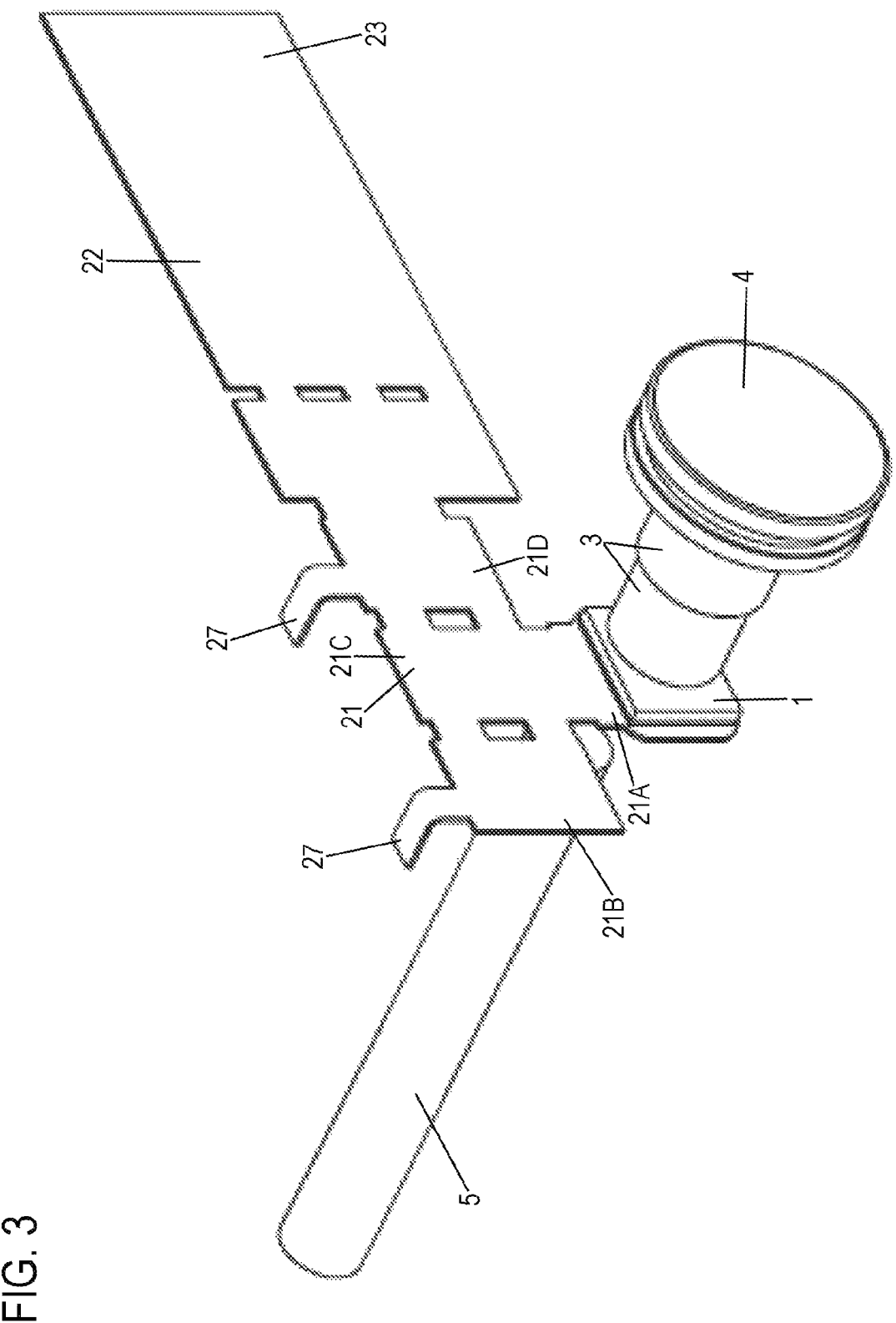
FIGS. 3 to 9 show the folding of the circuit board of the first embodiment.
Figure 4:
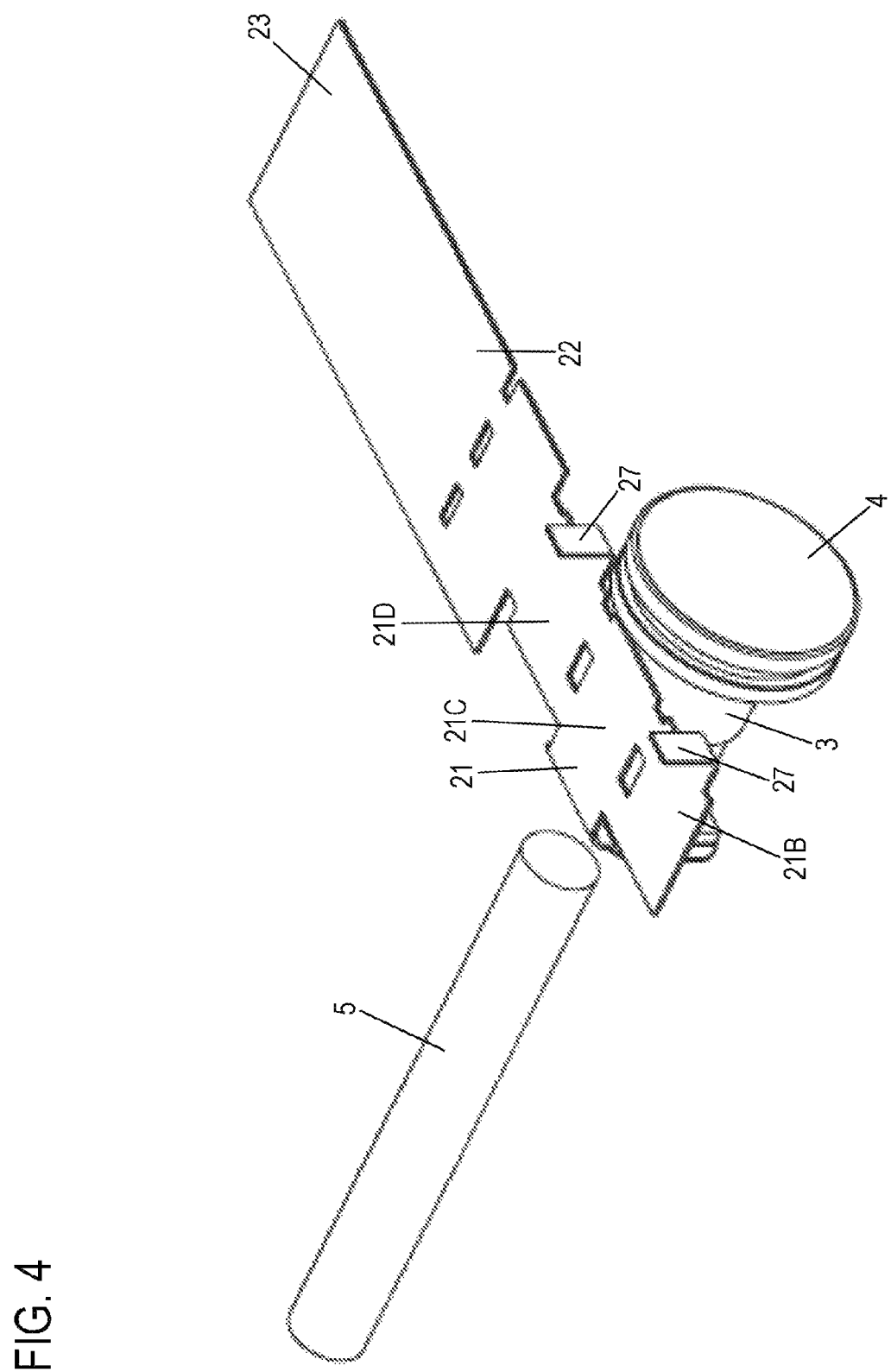
Figure 5:
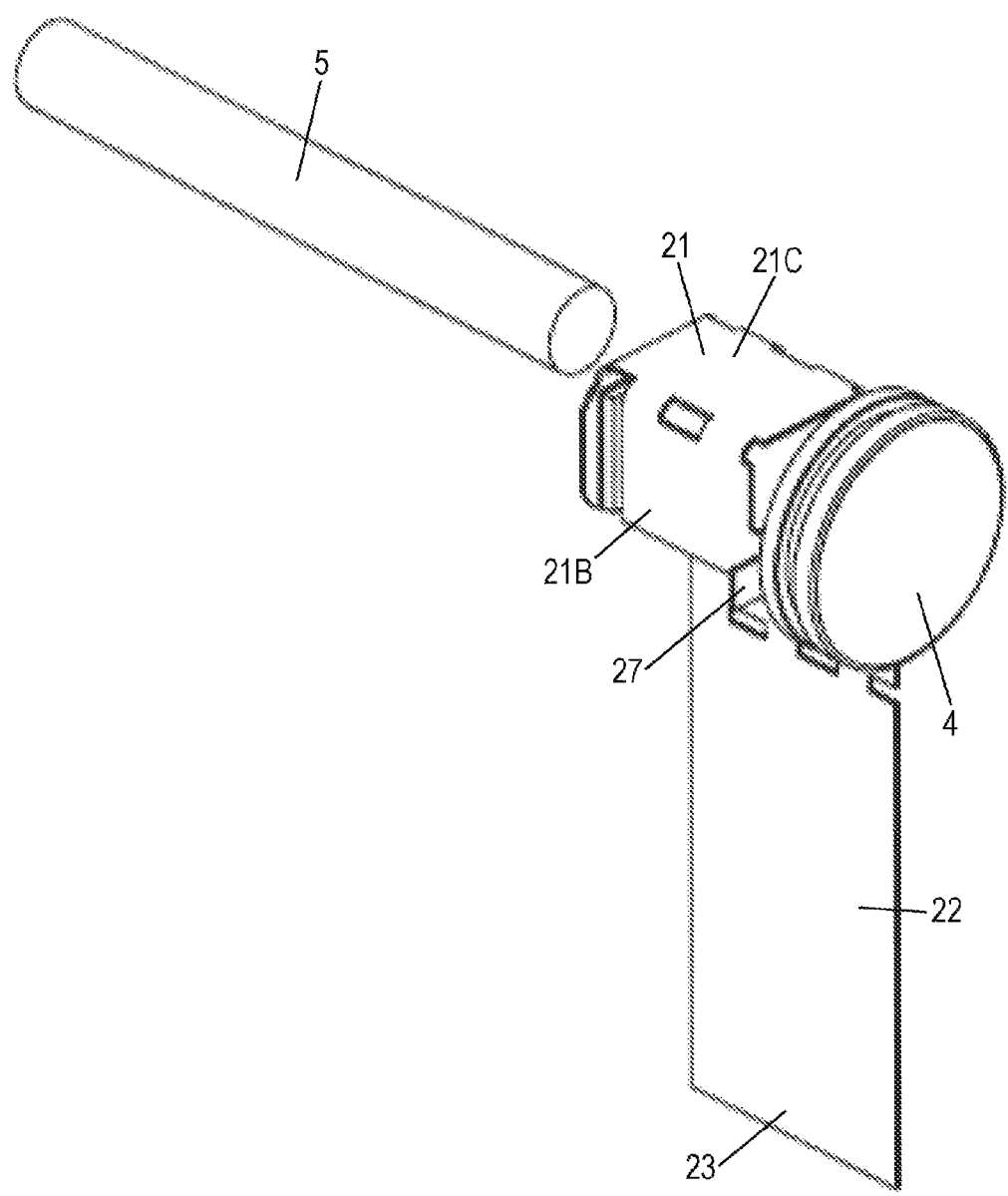

As shown in FIG. 2, the circuit board 2 has a main portion 21 and an edge portion 22. The edge portion 22 is separated from the main portion 21 by a fold edge. The fold edge between the main portion 21 and the edge portion 22 is suitable selected taking into consideration the components arranged on the circuit board and the folding geometry to be achieved. In FIG. 2, the fold edge between the main portion 21 and the edge portion 22 runs along a notch of the circuit board 2 such that the edge portion 22 is formed in a rectangular shape. The shapes of the main portion 21 and the edge portion 22 are to be understood merely as an example. The invention is not restricted to specific shapes.

The main portion 21 serves to supply current to the object. In the present embodiment, an image sensor 1, which acts as camera, is provided as object to be supplied with electric current. In the present embodiment, the image sensor 1 is arranged on the main portion 21. A mounting 3 as camera sleeve is arranged distally from the image sensor 1. The mounting 3 is cylindrically shaped. The mounting 3 extends in the longitudinal direction of the endoscope head 100. The lens 4 is arranged on the distal side of the mounting 3. Light is incident on the lens 4 and is guided inside the mounting 3 to the image sensor 1. Thus, the mounting 3 has a proximal side facing the image sensor 1, a distal side facing the lens 4, and a circumferential side pointing in the radial direction of the endoscope head 100.

The main portion 21 can have an arbitrary shape. In the present embodiment, the main portion 21 is formed from an arrangement region 21A for the image sensor 1, a first lateral region 21B, a central region 21C, and a second lateral region 21D. At the central region 21C, the arrangement region 21A for the image sensor 1, the first lateral region 21B and the second lateral region 21D are adjacent, these being foldable relative to the central region 21C. The first lateral region 21B and the second lateral region 21D adjoin the central region 21C such that they are opposite to each other. The arrangement region 21A adjoins the central region 21C on a side which differs from the side on which the first lateral region 21B and the second lateral region 21D adjoin the central region 21C.

On the first lateral region 21B and the second lateral region 21D, a flap 27 is respectively arranged on the side opposite the arrangement region 21A. The flap 27 can be used as a connection element for a power cable or as insertion element into an opening of the circuit board 2 so as to support the circuit board 2 to maintain a folded state. The flap 27 is to be understood as an example in this case. It can be arranged at any suitable position of the circuit board 2.

The edge portion 22 includes an end portion 23 on the side opposite the main portion 21.

The circuit board 2 can further include openings and notches.

As viewed from the image sensor 1, the circuit board 2 is folded in the distal direction.

The FIGS. 3 to 9 show the folding of the circuit board 2 of the first embodiment. The folding of the circuit board 2 is shown here as an example. According to the invention, the circuit board 2 is folded such that it extends at least partly relative to the location of the image sensor 1 in the distal direction of the endoscope head 100.

An example of folding the circuit board 2 is described below with reference to FIGS. 3 to 9.

On the circuit board 2, the image sensor 1 is arranged, e.g. soldered, on the arrangement region 21A. First, the flaps 27 are folded in the proximal direction. Then, the entire circuit board 2 except for the arrangement region 21A is folded in the distal direction, see FIG. 4. The central region 21C is thereby folded toward the mounting 3. Thus, the central region 21C extends parallel to the mounting 3. Thereafter, the first lateral region 21B is folded relative to the central region 21C toward the mounting 3.

Then, the second lateral region 21D is folded relative to the central region 21C toward the mounting 3. Hereby, the second lateral region 21D and the edge portion 22 are folded relative to the central region 21C. The first lateral region 21B and the second lateral region 21D thus also extend parallel to the mounting 3. In this state, the mounting 3 is covered on three sides of its circumferential side by the first lateral region 21B, the central region 21C and the second lateral region 21D, see FIG. 5.

Figure 6:
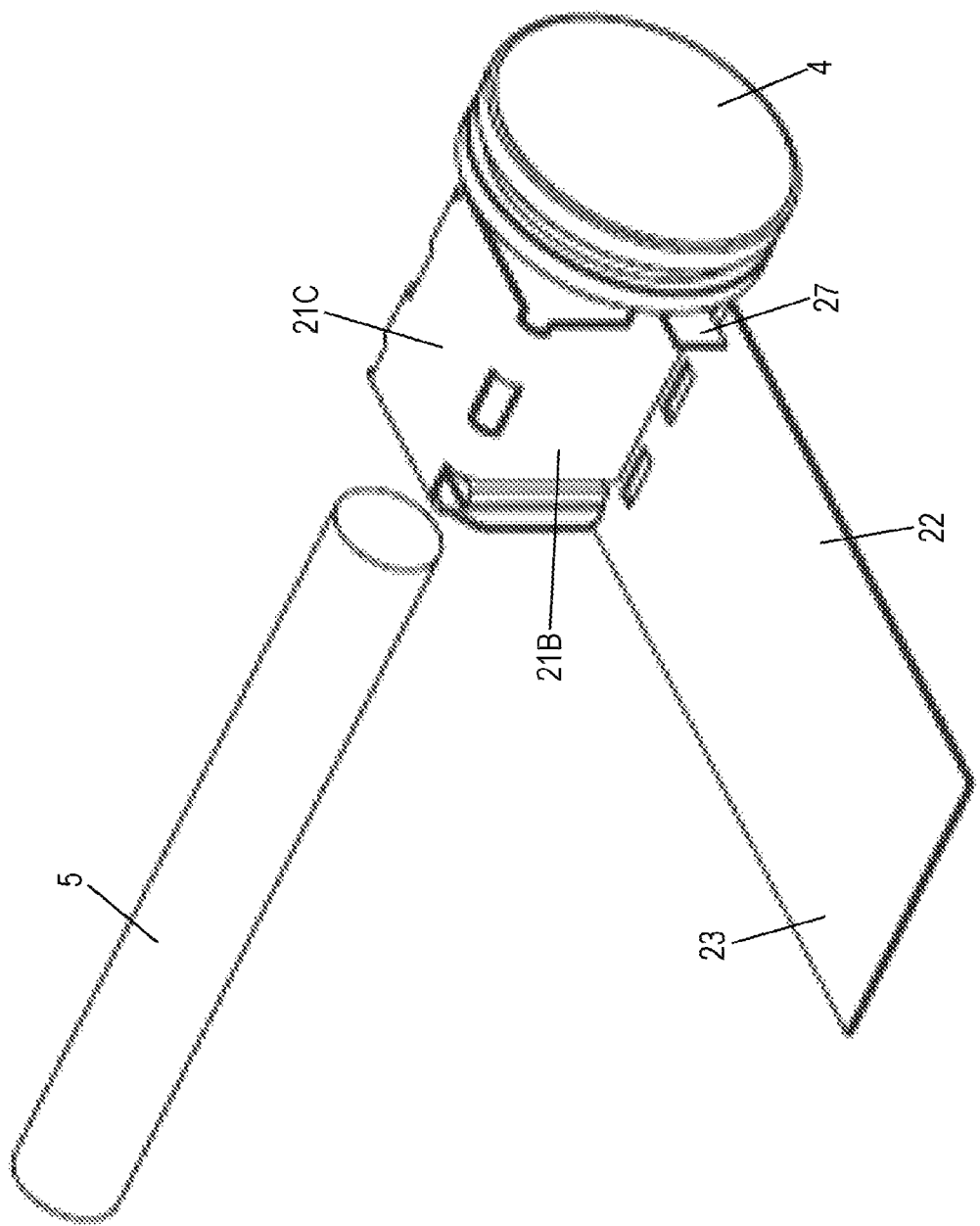

Thereafter, the edge portion 22 is folded relative to the second lateral region 21D such that the previously uncovered side of the circumferential side of the mounting 3 is covered by a portion of the edge portion 22, see FIG. 6. The portion of the edge portion 22 covering the mounting 3 is a portion adjacent to the fold line to the main portion 21.

Figure 7:
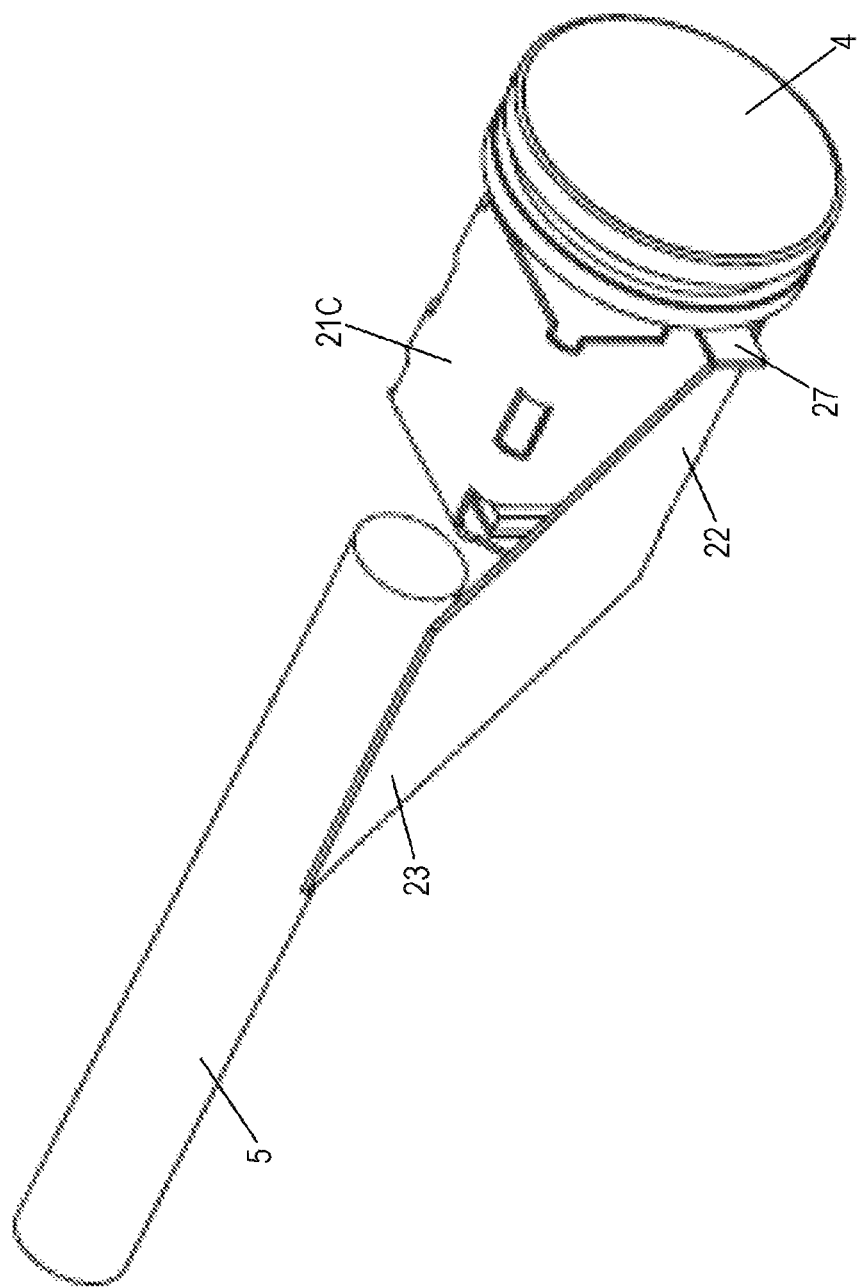

Then, the edge portion 22 is further folded relative to its portion of the edge portion 22 covering the mounting 3 such that the now folded portion of the edge portion 22 covers the first lateral region 21B, see FIG. 7. The remaining portion of the edge portion 22 including the end portion 23 is further folded in the same direction. In this way, the edge portion 22 covers the central region 21C and the second lateral region 21D. The end portion 23 hereby acts as an electronic shielding that covers the parts of the main portion 21 which are to be shielded electronically. Thus, the electronic shielding of the main portion 21 can be realized in a simple and cost-effective manner by folding a part of the circuit board, namely the end portion 23, to the main portion 21 and the part of the circuit board being in contact with the main portion, see FIGS. 8 and 9.

In this connection, the portions of the circuit board 2 can be folded such that they form fold edges to each other. The circuit board 2 can also be bent such that it does not form fold edges so that basically a round cylindrical shape of the bent or wound circuit board 2 results. The term "folded" is also intended to include winding without formation of fold edges.

Furthermore, not all of the main portion 21 need be covered by parts of the edge portion 22. For example, the second lateral region 21D can remain uncovered.

Effect of the First Embodiment

Since the circuit board 2 extends relative to the image sensor 1 in the distal direction, the space proximally from the image sensor 1 can remain free of the circuit board 2. Thus, the circuit board 2 can be installed in a space-saving manner.

The circuit board 2 surrounds the image sensor 1, which it supplies with current, in the radial direction and protects it.

The circuit board 2 can be assigned further functions. For example, the circuit board 2 can be used to support the mounting 3 that functions as camera sleeve.

Second Embodiment

Below, with reference to FIGS. 10 and 11, a second embodiment of the present invention is described.

Figure 10:
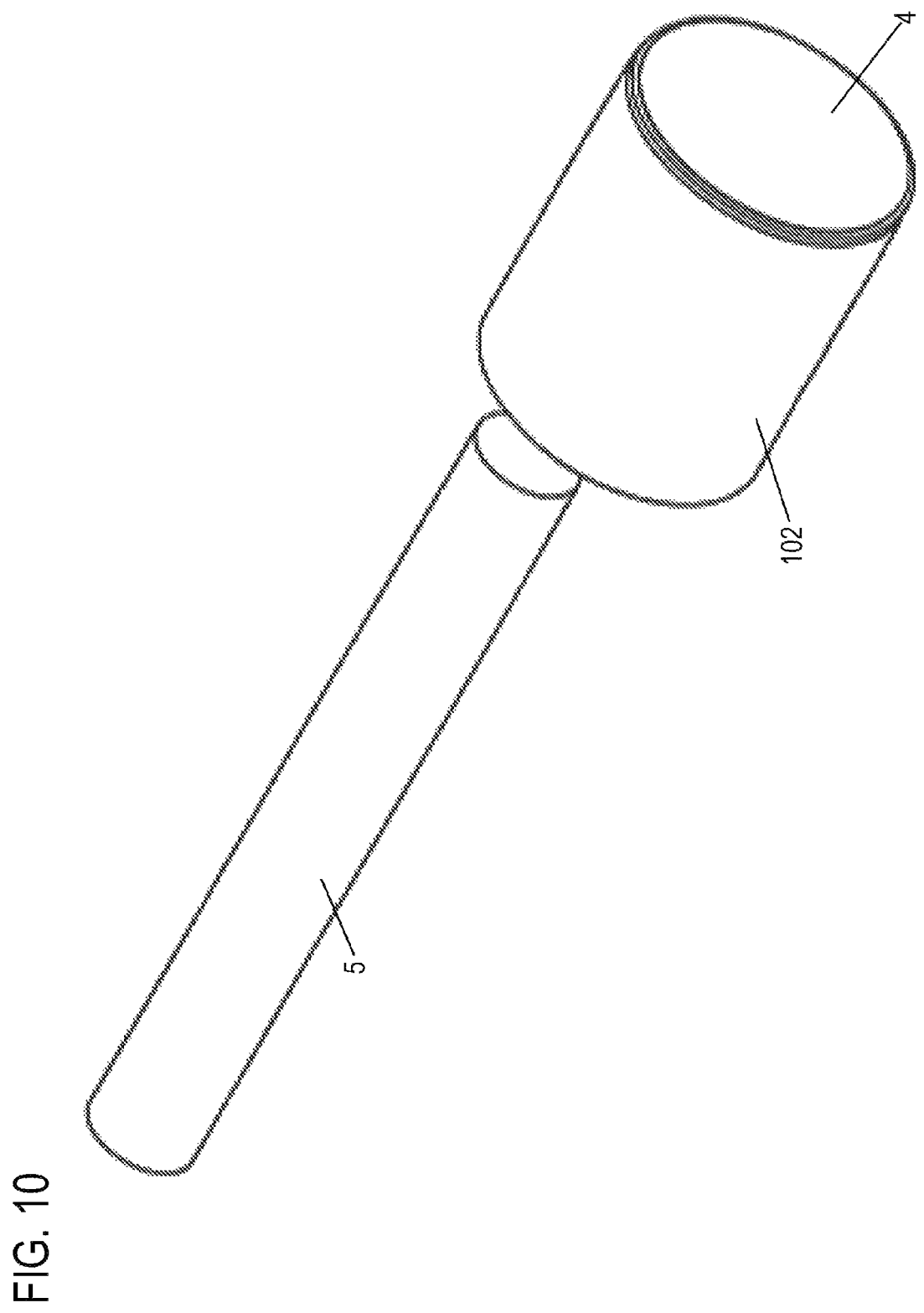
FIG. 10 shows a schematic perspective view of an endoscope head of a second embodiment of the present invention.

FIG. 10 shows that a circuit board 102 has been folded such that the circuit board 102 surrounds an image sensor not shown and a mounting not shown as in the first embodiment.

Here, the folded circuit board 102 extends to the distal side to such an extent that it laterally surrounds the lens 4. The lateral edge of the lens 4 is thus surrounded by an inner circumference of the circuit board 102. The distal end of the circuit board 102 is aligned with the distal side of the lens 4. The edge portion and the main portion of the circuit board 102 form a closed circle in cross-section, which extends around a lens mounting of the lens 4. The distal portion of the circuit board 102 can thereby itself form the lens mounting.

Figure 11:
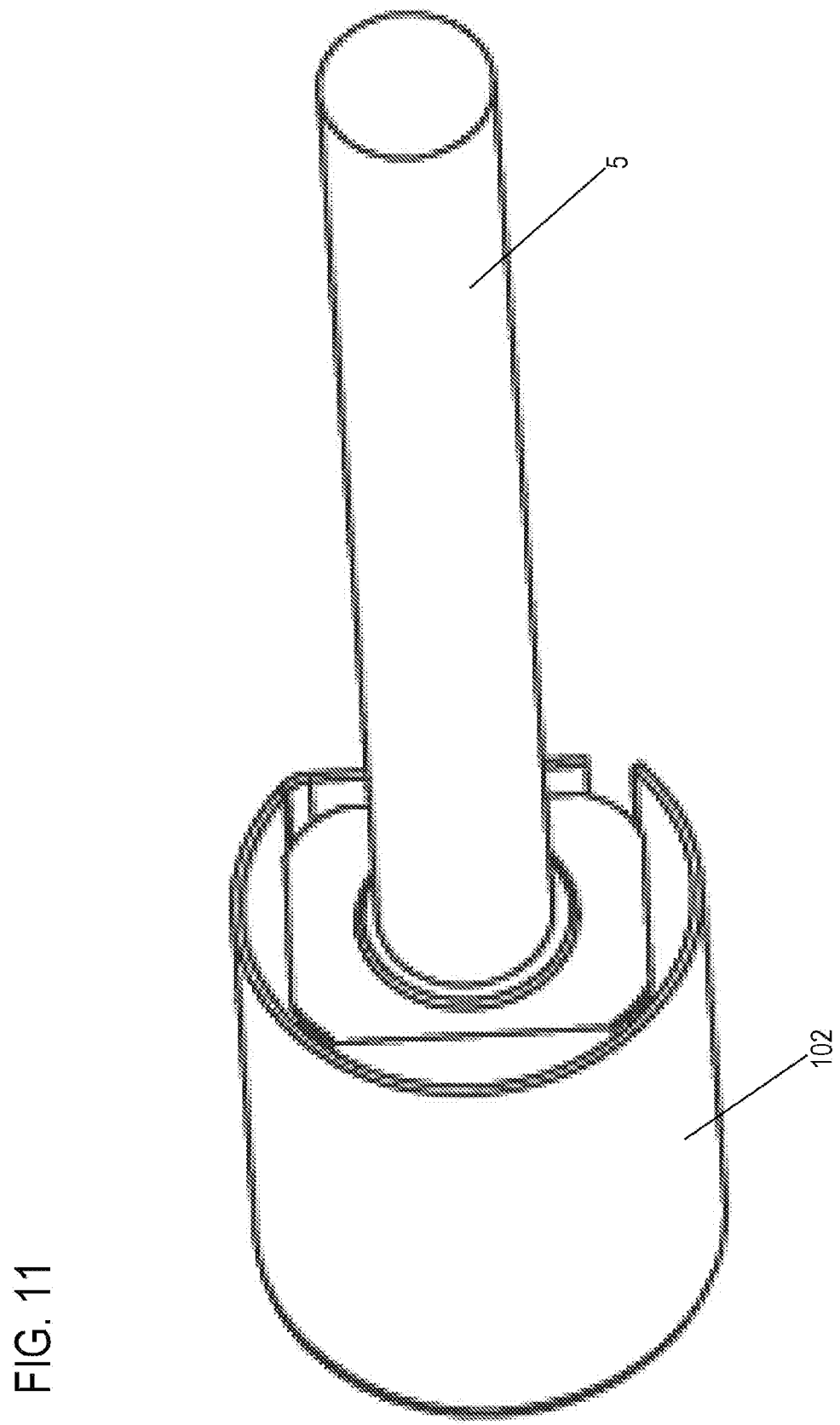
FIG. 11 shows a schematic perspective view of the endoscope head of the second embodiment from the proximal side.

FIG. 11 shows an alternative in which the circuit board 102 has been folded such that the circuit board 102 does not entirely surround the circumference of the mounting.

In this embodiment, the circuit board 102 additionally protects and stabilizes the lens 4.

Third Embodiment

Below, with reference to FIG. 12, a third embodiment of the present invention is described.

Figure 12:
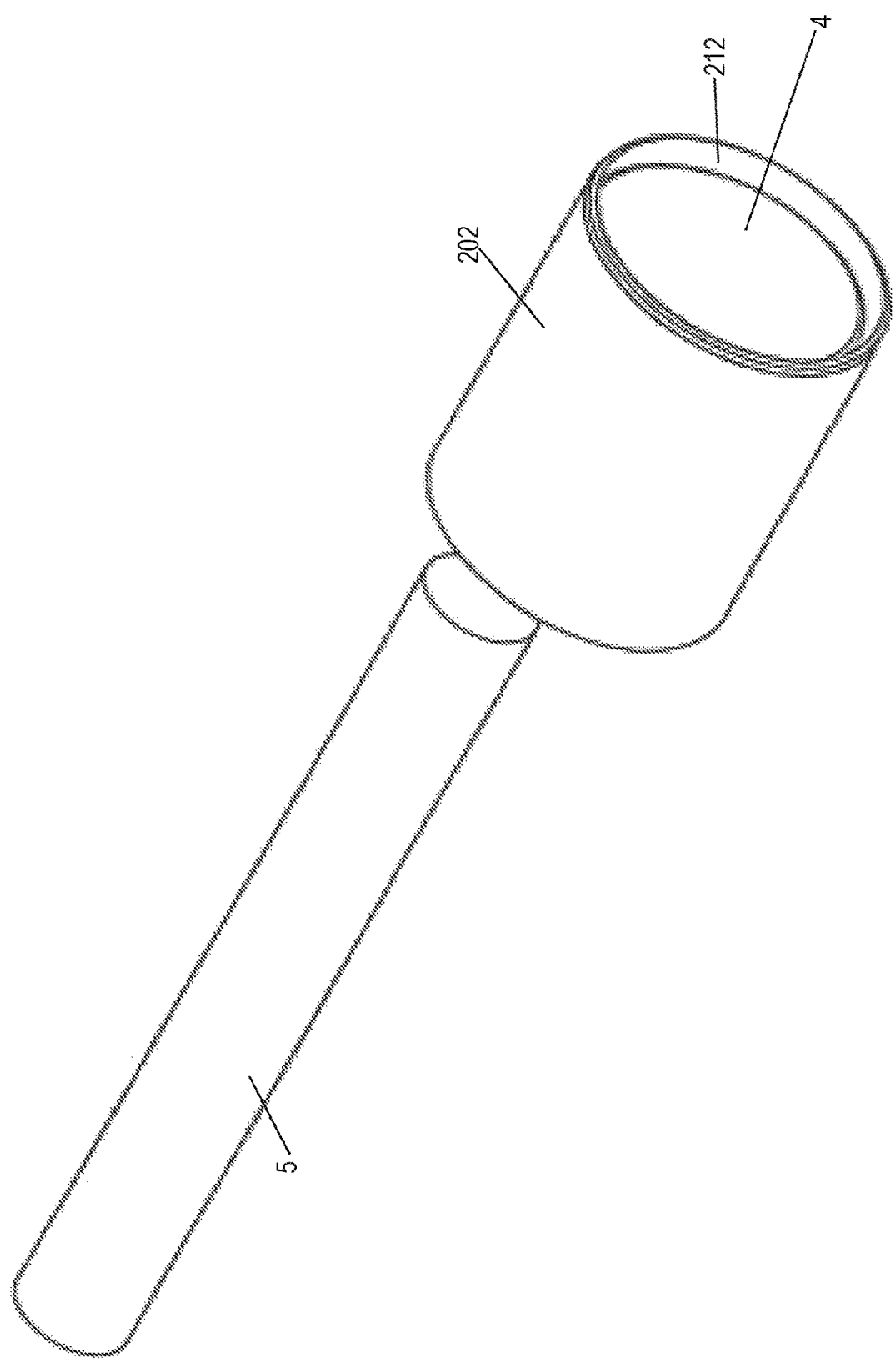
FIG. 12 shows a schematic perspective view of an endoscope head of a third embodiment of the present invention.

FIG. 12 shows that a circuit board 202 has been folded such that the circuit board 202 surrounds an image sensor not shown and a mounting not shown as in the first embodiment.

In contrast to the second embodiment, the folded circuit board 202 extends to the distal side to such an extent that it laterally surrounds the lens 4 and protrudes beyond the lens 4. In other words, the distal portion of the folded circuit board 202 projects beyond the distal side of the lens 4. The region of the circuit board 202 extending from the distal side of the lens 4 in the distal direction acts as an optical shielding for the lens 4 here. This optical shielding shields an unexpected radial incidence of light of a light source which is laterally from the lens 4. Thus, only light from the distal side reaches the lens 4.

In this embodiment, the circuit board 202 additionally functions as optical shielding for the lens 4.

Alternatives

The explained embodiments can be suitably combined, provided that this does not result in any technical contradiction.

Figure 8:
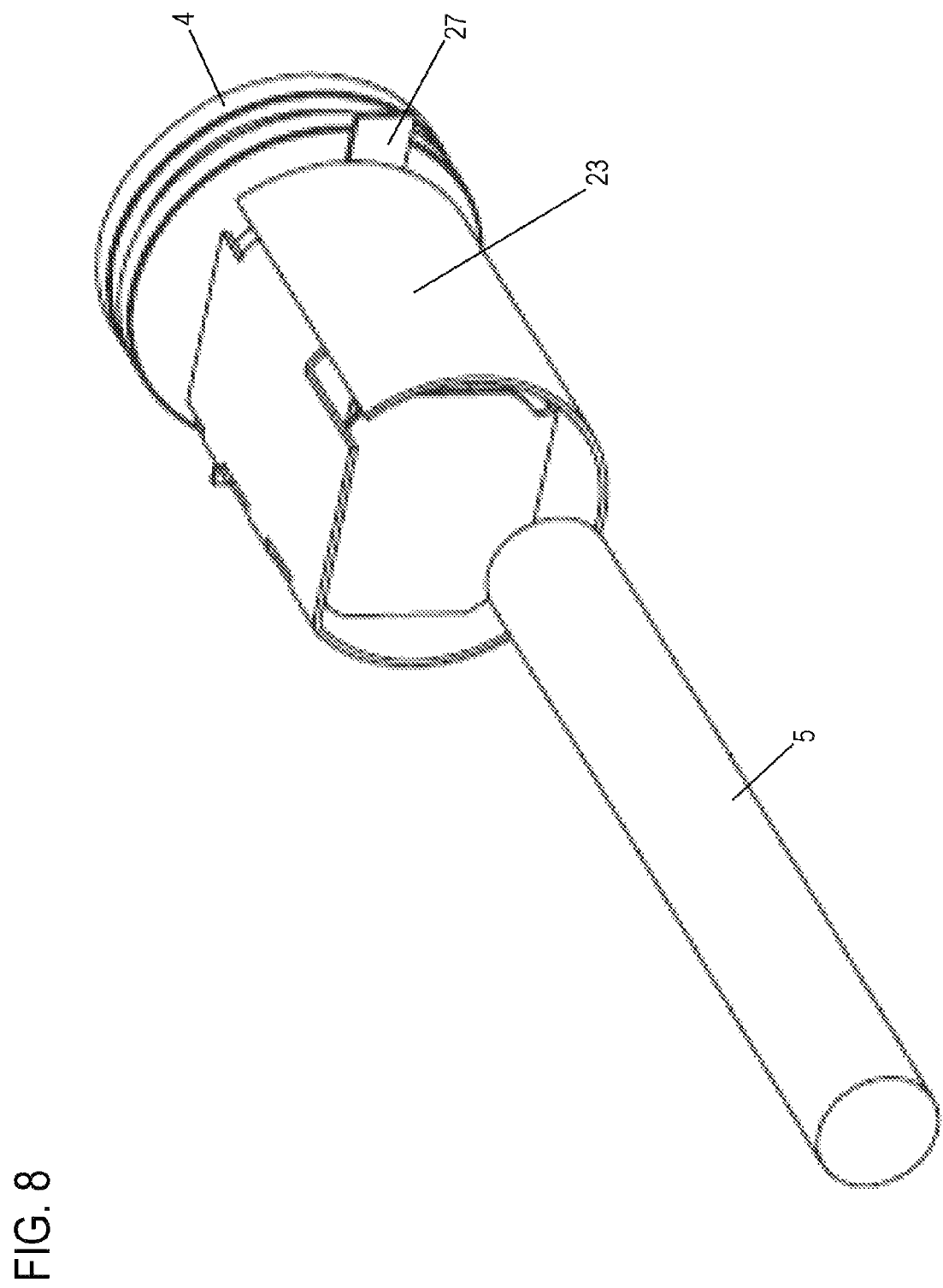
Figure 9:
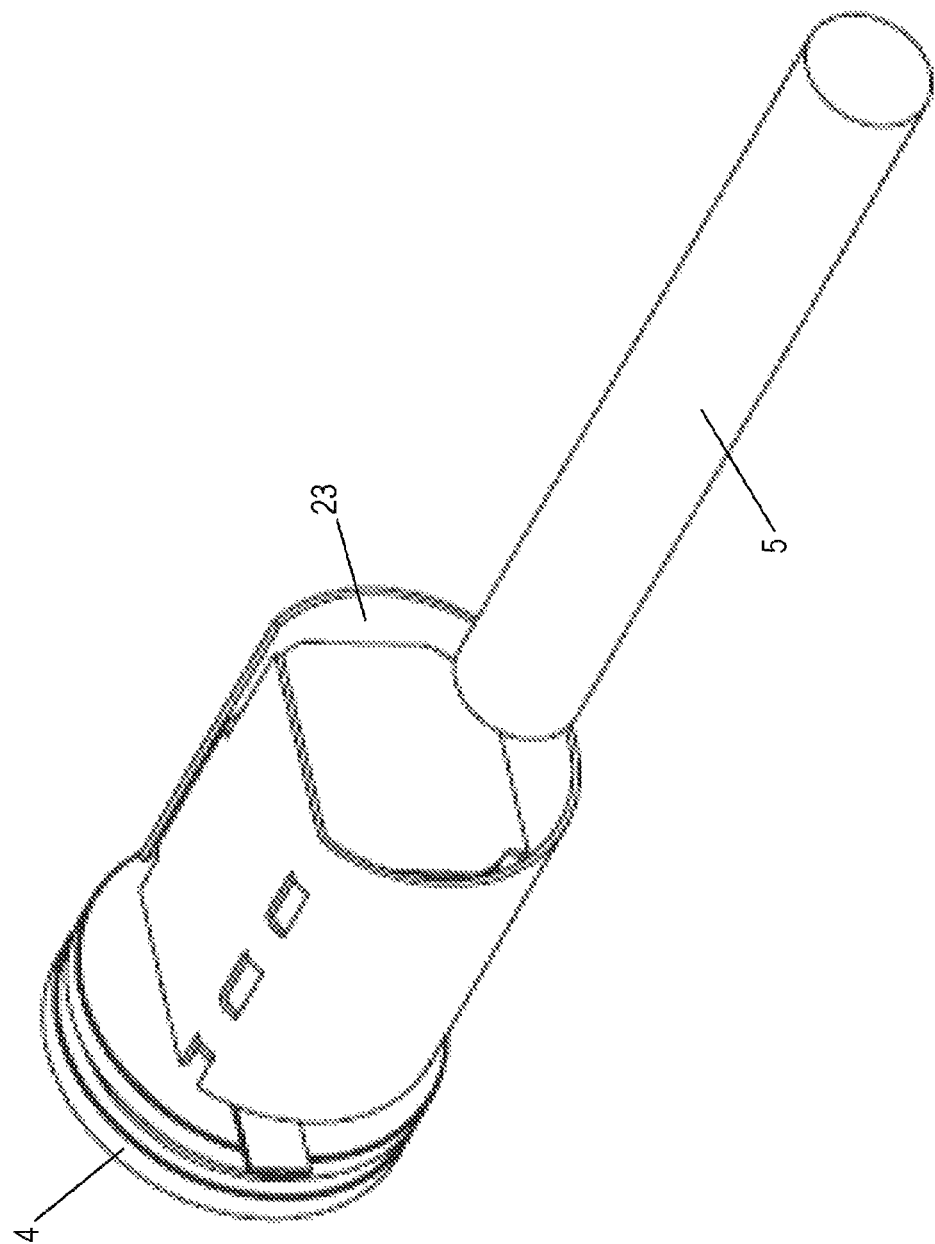

The folded (or wound) circuit board 2 can have a shape that entirely surrounds the mounting 3 at the circumferential side of the mounting 3, as shown in FIGS. 8 and 9.

Alternatively, the circuit board 2 can be folded (or wound) such that a portion of the circumferential side of the mounting 3 is not covered by the circuit board 2. This alternative can also provide stability to the camera sleeve.

In the embodiments, the circuit board 2 can be used to support the mounting 3 that functions as camera sleeve. In an alternative, the mounting 3 can be omitted. The inner peripheral side of the folded (or wound) circuit board 2 can perform the function of the mounting 3 as camera sleeve.

In another alternative, the folded (or wound) circuit board 2 can even form a housing of the endoscope head 100 itself. Thus, in a specific alternative case, the folded (or wound) circuit board 2 can even form the outer periphery of the endoscope head 100.

The present invention is applicable to each type of endoscope.

LIST OF REFERENCE SIGNS 1 image sensor
2 circuit board
3 camera sleeve
4 lens
5 cable
21 main portion
21A arrangement region for image sensor
21B first lateral region
21C central region
21D second lateral region
22 edge portion
23 end portion; electronic shielding
27 flap
100 endoscope head
102 circuit board
202 circuit board
212 optical shielding

The invention claimed is:

1. An endoscope comprising
an image sensor, which is to be supplied with electric current and which is to capture an image, in an endoscope head of the endoscope, and
a circuit board for the image sensor, wherein:
the circuit board includes a main portion for the image sensor, and an edge portion,
the circuit board extends from the image sensor in the distal direction of the endoscope head,
the edge portion is connected to the main portion on a fold edge and includes an end portion on the side opposite the main portion,
the end portion is folded such that it is in contact with the main portion to form an electronic shielding, and
the edge portion and the main portion form a closed circle in cross-section, and extend around the lens.

2. The endoscope according to claim 1, wherein
the image sensor is arranged on the circuit board.

3. The endoscope according to claim 1, wherein
the circuit board extends to a location distally from the image sensor.

4. The endoscope according to claim 1, wherein
the circuit board is folded, and
at least a portion of the circuit board is located proximally from the image sensor.

5. The endoscope according to claim 1, comprising
a lens arranged on the distal side of the image sensor,
wherein the circuit board at least partly surrounds the lens.

6. The endoscope according to claim 5, wherein
the circuit board protrudes beyond the lens in the distal direction.

7. The endoscope according to claim 6, wherein
the circuit board forms an optical shielding between the lens and a light source that acts on the distal end of the endoscope head to shield a light irradiation of the light source to the lens.

8. The endoscope according to claim 1, wherein
the circuit board forms a housing of the endoscope head.

* * * * *